United States Patent
Djupesland

(10) Patent No.: US 8,555,877 B2
(45) Date of Patent: *Oct. 15, 2013

(54) NASAL DELIVERY DEVICE

(75) Inventor: Per Gisle Djupesland, Oslo (NO)

(73) Assignee: OptiNose AS, Oslo (NO)

( * ) Notice: Subject to any disclaimer, the term of this patent is extended or adjusted under 35 U.S.C. 154(b) by 0 days.
This patent is subject to a terminal disclaimer.

(21) Appl. No.: 11/445,812

(22) Filed: Jun. 2, 2006

(65) Prior Publication Data

US 2006/0225732 A1    Oct. 12, 2006

Related U.S. Application Data

(63) Continuation of application No. 10/813,326, filed on Mar. 30, 2004, now Pat. No. 8,327,844, which is a continuation of application No. 09/700,532, filed as application No. PCT/IB00/00273 on Mar. 3, 2000, now Pat. No. 6,715,485.

(30) Foreign Application Priority Data

Mar. 3, 1999   (GB) .................................... 9904906.6
May 19, 1999   (GB) .................................... 9911686.5

(51) Int. Cl.
| A61M 15/00 | (2006.01) |
| A61M 15/08 | (2006.01) |
| A61M 16/00 | (2006.01) |
| A61M 31/00 | (2006.01) |
| A61M 13/00 | (2006.01) |
| A61M 11/00 | (2006.01) |
| A62B 7/00 | (2006.01) |

(52) U.S. Cl.
USPC ............ 128/203.22; 128/200.23; 128/203.15; 128/203.18; 128/207.18

(58) Field of Classification Search
USPC ............. 128/202.22, 203.12, 203.15, 203.21, 128/203.22, 203.24, 200.24, 204.11, 128/204.12, 200.23, 203.18, 207.18; 482/13; 11/202.22, 203.12, 203.15, 11/203.21, 203.22, 203.24, 200.24, 11/204.11, 204.12
See application file for complete search history.

(56) References Cited

U.S. PATENT DOCUMENTS

| 39,678 A | 8/1863 | Russell |
| 419,942 A | 1/1890 | Harding |

(Continued)

FOREIGN PATENT DOCUMENTS

| CA | 2271131 A | 5/1998 |
| CA | 2155956 A | 4/2005 |

(Continued)

OTHER PUBLICATIONS

Desmopressin Acetate Rhinal Tube Patient Instruction Guide, website page 2002, 2 pages, Ferring Pharmaceuticals, Malmo, Sweden.
U.S. Appl. No. 11/816,984, filed Aug. 23, 2007, Djupesland.
U.S. Appl. No. 12/161,466, filed Jul. 18, 2008, Djupesland.
U.S. Appl. No. 12/279,285, filed Aug. 13, 2008, Djupesland.
U.S. Appl. No. 12/279,291, filed Aug. 13, 2008, Djupesland.

(Continued)

*Primary Examiner* — Gary Jackson
*Assistant Examiner* — Michael Mendoza
(74) *Attorney, Agent, or Firm* — Lihua Zheng; Mary S Consalvi; Proskauer Rose LLP

(57) ABSTRACT

A delivery device (20, 22) for and a method of delivering a substance to the nasal airway (1) of a subject, in particular the posterior region of the nasal airway, the delivery device comprising: a closure unit for causing the closure of the oropharyngeal velum of the subject; and a delivery unit for delivering a gas flow entraining a substance to one of the nostrils of the subject at such a driving pressure as to flow around the posterior margin of the nasal septum and out of the other nostril of the subject, wherein the delivery unit comprises a nosepiece (30, 40, 58, 82, 102, 132) which includes an outlet through which the gas flow is in use delivered to the one nostril and a sealing member for sealing the one nostril to the outlet such as in use to prevent the escape of the gas flow through the one nostril.

11 Claims, 5 Drawing Sheets

(56) References Cited

U.S. PATENT DOCUMENTS

Figure 1:
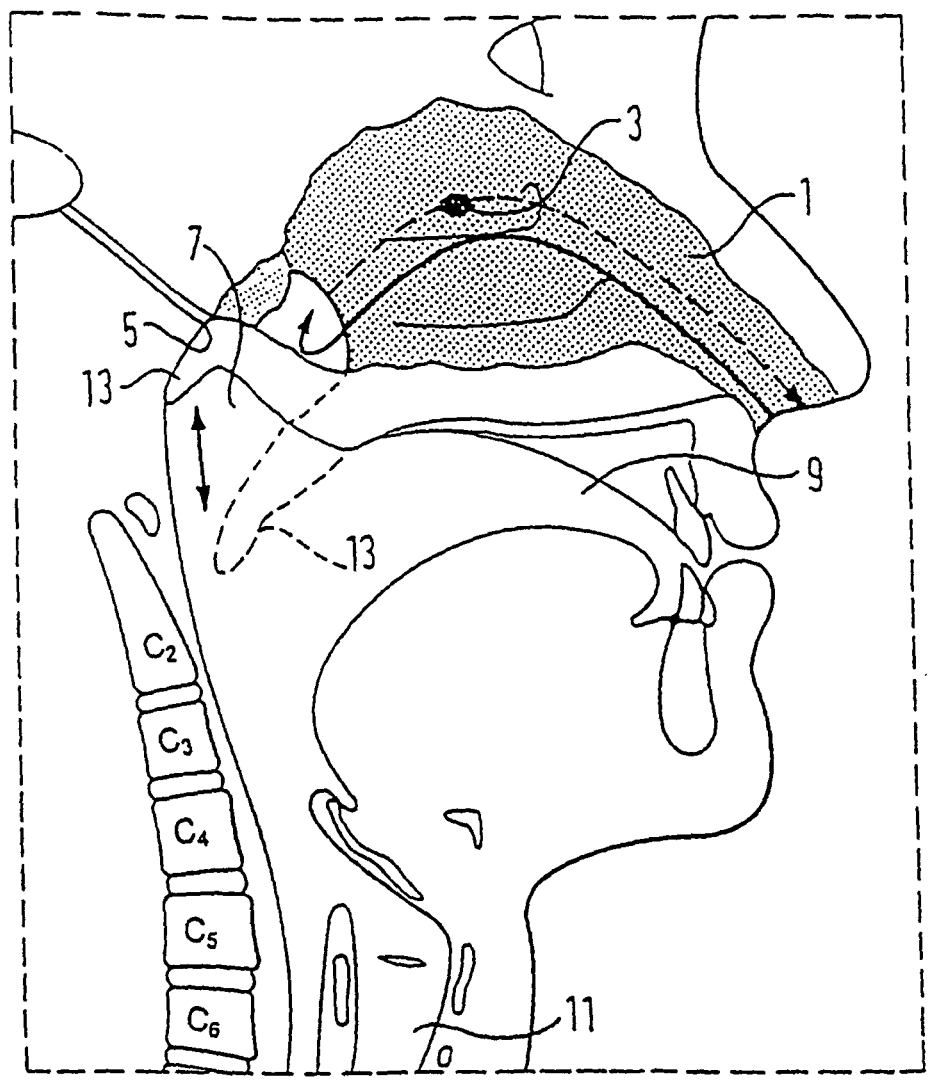

| | | | |
|---|---|---|---|
| 429,321 A | 6/1890 | Ramey | |
| 605,436 A | 6/1898 | Kellogg | |
| 658,436 A | 9/1900 | Groth | |
| 707,445 A | 8/1902 | McCulloch | |
| 723,738 A | 3/1903 | Schulte | |
| 746,749 A | 12/1903 | Seidel | |
| 781,428 A | 1/1905 | Hutcnins | |
| 794,641 A | 7/1905 | Ramey | |
| 867,827 A | 10/1907 | McCulloch | |
| 902,832 A | 11/1908 | Philbrook | |
| 1,375,325 A | 4/1921 | Schaefer | |
| 1,540,274 A | 6/1925 | Moore | |
| 1,873,160 A | 8/1932 | Sturtevant | |
| 2,021,332 A | 11/1935 | Silten | |
| 2,086,588 A | 7/1937 | Tobin | |
| 2,223,611 A | 12/1940 | Gross | |
| 2,470,297 A | 5/1949 | Fields | |
| 2,693,805 A | 11/1954 | Taplin | |
| 3,847,145 A | 11/1974 | Grossan | |
| 3,888,252 A | 6/1975 | Side et al. | |
| 3,949,939 A | 4/1976 | Brown | |
| 4,216,768 A | 8/1980 | Jack | |
| 4,265,236 A | 5/1981 | Pacella | |
| 4,660,555 A * | 4/1987 | Payton | 128/207.18 |
| 4,674,494 A | 6/1987 | Wiencek | |
| 4,889,114 A | 12/1989 | Kladders | |
| 4,919,128 A | 4/1990 | Kopala et al. | |
| 4,940,051 A | 7/1990 | Lankinen | |
| 5,046,493 A | 9/1991 | Kropkowski | |
| 5,167,242 A | 12/1992 | Turner et al. | |
| 5,373,841 A | 12/1994 | Kyllonen et al. | |
| 5,375,593 A | 12/1994 | Press | |
| 5,472,002 A | 12/1995 | Covarrubias | |
| 5,487,378 A | 1/1996 | Robertson et al. | |
| 5,645,051 A | 7/1997 | Schultz | |
| 5,655,523 A | 8/1997 | Hodson et al. | |
| 5,666,948 A * | 9/1997 | Matson | 128/200.23 |
| 5,669,378 A | 9/1997 | Pera | |
| 5,694,920 A | 12/1997 | Abrams et al. | |
| 5,735,263 A | 4/1998 | Rubsamen | |
| 5,752,510 A | 5/1998 | Goldstein | |
| 5,797,392 A | 8/1998 | Keldmann | |
| 5,829,435 A | 11/1998 | Rubsamen | |
| 5,850,833 A | 12/1998 | Kotliar | |
| 5,899,202 A | 5/1999 | Ohki et al. | |
| 5,904,140 A | 5/1999 | McGoogan | |
| 5,937,852 A | 8/1999 | Butler et al. | |
| 6,012,454 A | 1/2000 | Hodson et al. | |
| 6,019,100 A | 2/2000 | Alving | |
| 6,029,662 A | 2/2000 | Marcon | |
| 6,073,628 A | 6/2000 | Butler et al. | |
| 6,074,673 A | 6/2000 | Guillen | |
| 6,125,844 A | 10/2000 | Samiotes | |
| 6,145,503 A | 11/2000 | Smith | |
| 6,182,660 B1 | 2/2001 | Hopper | |
| 6,581,592 B1 | 6/2003 | Bathe et al. | |
| 6,715,485 B1 | 4/2004 | Djupesland | |
| 7,347,201 B2 | 3/2008 | Djupesland | |
| 7,377,901 B2 | 5/2008 | Djupesland et al. | |
| 7,481,218 B2 | 1/2009 | Djupesland | |
| 7,543,581 B2 | 6/2009 | Djupesland | |
| 2004/0112378 A1 | 6/2004 | Djupesland | |
| 2004/0112379 A1 | 6/2004 | Djupesland | |
| 2004/0182388 A1 | 9/2004 | Djupesland | |
| 2005/0028812 A1 | 2/2005 | Djupesland | |
| 2005/0072430 A1 | 4/2005 | Djupesland | |
| 2005/0235992 A1 | 10/2005 | Djupesland | |
| 2006/0096589 A1 | 5/2006 | Djupesland | |
| 2006/0169278 A1 | 8/2006 | Djupesland | |
| 2006/0219240 A1 | 10/2006 | Djupesland | |
| 2006/0219241 A1 | 10/2006 | Djupesland | |
| 2006/0231094 A1 | 10/2006 | Djupesland | |
| 2007/0039614 A1 | 2/2007 | Djupesland | |
| 2007/0125371 A1 | 6/2007 | Djupesland | |
| 2007/0186927 A1 | 8/2007 | Djupesland et al. | |
| 2008/0161771 A1 | 7/2008 | Djupesland | |
| 2008/0163874 A1 | 7/2008 | Djupesland | |
| 2008/0221471 A1 | 9/2008 | Djupesland | |
| 2008/0223363 A1 | 9/2008 | Djupesland | |
| 2008/0289629 A1 | 11/2008 | Djupesland | |
| 2009/0101146 A1 | 4/2009 | Djupesland | |

FOREIGN PATENT DOCUMENTS

| | | |
|---|---|---|
| DE | 3018691 A | 11/1981 |
| EP | 0341967 A | 11/1989 |
| EP | 0634186 A | 1/1995 |
| EP | 0695561 A | 2/1996 |
| FR | 2 638 361 | 5/1990 |
| GB | 408856 | 4/1934 |
| GB | 2270293 A | 3/1994 |
| HU | 215018 B | 7/1995 |
| HU | 213060 B | 1/1996 |
| SE | 8102793-0 | 11/1981 |
| WO | WO-96/22802 | 8/1996 |
| WO | WO-97/05918 | 2/1997 |
| WO | WO-98/53869 | 12/1998 |

OTHER PUBLICATIONS

U.S. Appl. No. 12/281,547, filed Sep. 3, 2008, Djupesland.
U.S. Appl. No. 12/281,894, filed Sep. 5, 2008, Djupesland.
U.S. Appl. No. 12/293,972, filed Sep. 22, 2008, Djupesland.
U.S. Appl. No. 12/298,292, filed Oct. 23, 2008, Djupesland.
U.S. Appl. No. 12/303,667, filed Dec. 5, 2008, Djupesland.
U.S. Appl. No. 12/375,115, filed Jan. 26, 2009, Djupesland.
U.S. Appl. No. 12/516,399, filed May 27, 2009, Djupesland.
U.S. Appl. No. 12/516,401, filed May 27, 2009, Djupesland.
U.S. Appl. No. 12/516,404, filed May 27, 2009, Djupesland.
U.S. Appl. No. 12/594,361, filed Oct. 2, 2009, Djupesland et al.
U.S. Appl. No. 12/594,365, filed Oct. 2, 2009, Djupesland et al.
Abstract P028, "A Novel Nasal Powder Device Improves Delivery to the Nasal Mucosa Innervated by the Trigeminal Nerve. A New Avenue to Therapeutic Success in Migraine?" in Program Abstracts from the 14th Congress of the International Headache Society, Sep. 10-13, 2009, Philadelphia, PA, published *Cephalalgia*, 29 (Suppl. 1) (2009).
Aggarwal et al., "The assessment of topical nasal drug distribution," Clin. Otolaryngol. 29, 201-205 (2004).
Chiarello "Bi-directional nasal device delivery drug on exhalation," Pharmaceutical Technology (Sep. 2004).
Djupesland "Who nose how far nasal delivery can go," European Pharmaceutical Contractor, (Autumn 2003).
Djupesland et al., "Bi-directional nasal drug delivery," *Innovations in Pharmaceutical Technology*, pp. 92-102 (2004).
Djupesland et al., "Breath Actuated Device Improves Delivery to Target Sites Beyond the Nasal Valve," Laryngoscope 116:446-472 (Mar. 2006).
Djupesland et al., "A Novel Nasal Powder Device Improves Delivery to the Nasal Mucosa Innervated by the Trigeminal Nerve. A New Avenue to Therapeutic Success in Migraine?" Poster (© 2009).
Dubin "Nothing to sneeze at," PFQ Magazine (Jun./Jul. 2002).
Fertil Steril. Nov. 1976;27(11):1246-9.
Harris et al., "Nasal administration of desmopressin by spray and drops," J. Pharm. Pharmacol., 39:932-934 (1987).
International Search Report for International App. No. PCT/IB00/00273, Mailed Aug. 16, 2000 (4 pages).
International Preliminary Report on Patentability for International App. No. PCT/IB00/00273 (8 pages).
OnDrugDelivery, "Breath-Actuated Bi-Directional Delivery Sets the Nasal Market on a New Course," 3rd issue Nasal, pp. 20-23 (Aug. 10, 2005).
Opposition Proceedings for European Patent No. 1161274.
Ohki et al., "Dimensions and Resistances of the Human Nose: Racial Differences," Laryngoscope, vol. 101, pp. 276-278 (Mar. 1991).
Thorsson et al., "Nasal Distribution of Budesonide Inhaled via a Powder Inhaler," Rhinology, 31, 7-10 (1993).

* cited by examiner

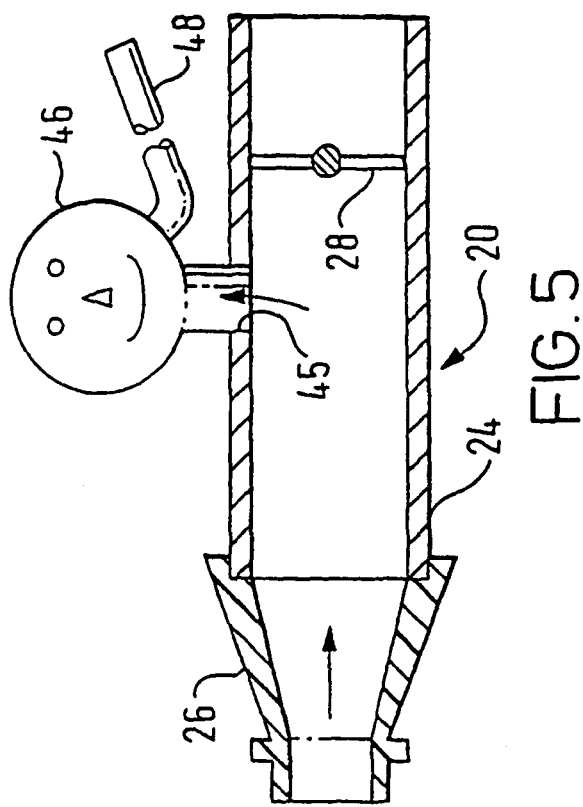
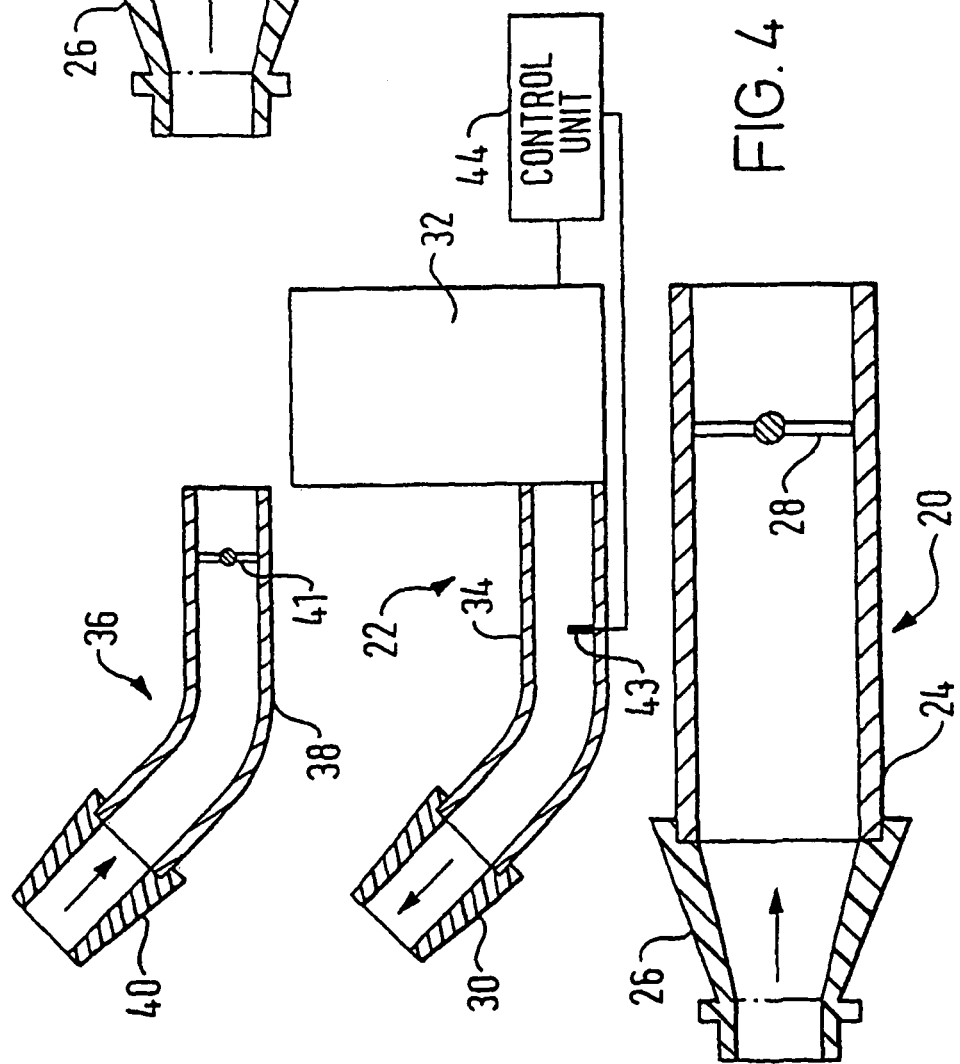
FIG. 5
FIG. 4

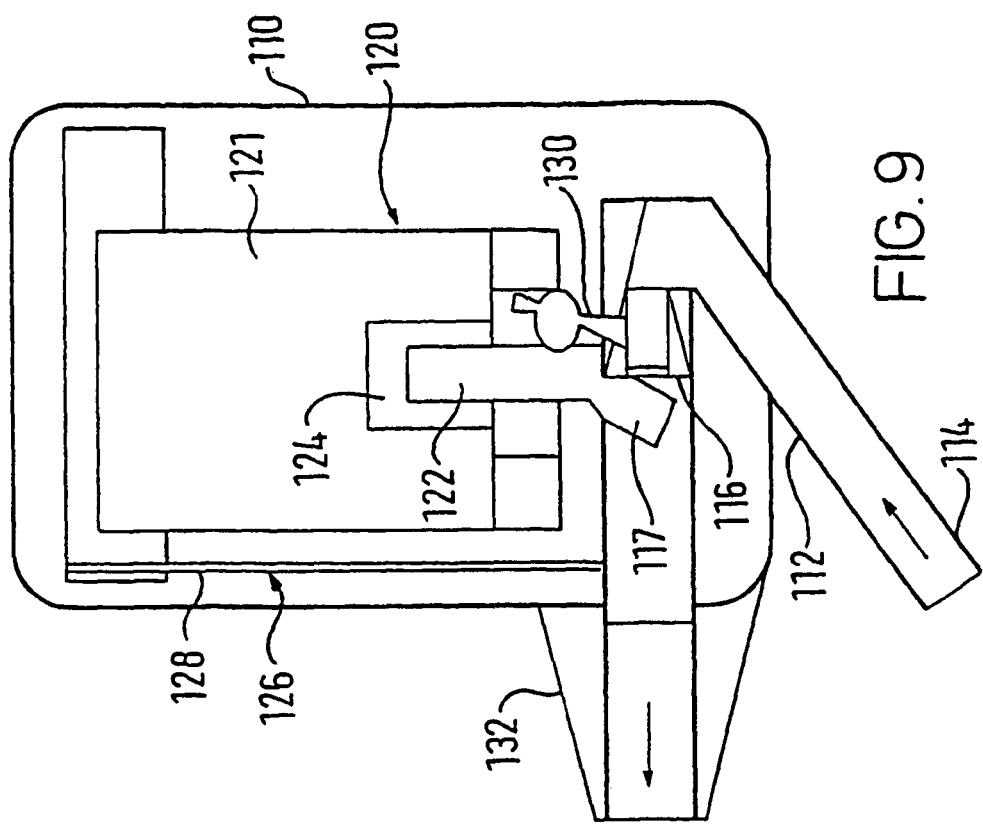
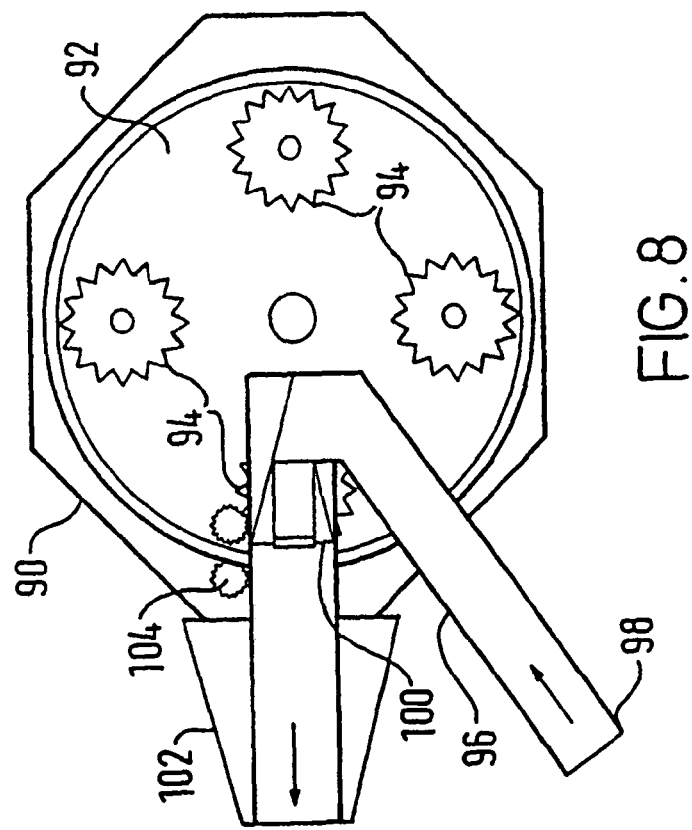

NASAL DELIVERY DEVICE

RELATED APPLICATION DATA

This application is a continuation of application Ser. No. 10/813,326, now U.S. Pat. No. 8,327,844, filed Mar. 30, 2004, which is a continuation of application Ser. No. 09/700,532, filed Nov. 15, 2000, now U.S. Pat. No. 6,715,485, which is a national phase of International Application No. PCT/IB00/00273, filed Mar. 3, 2000, and published in the English language under Publication No. WO 00/51672, both of which applications are hereby incorporated herein by reference in their entireties.

FIELD OF THE INVENTION

The present invention relates to a delivery device for and a method of delivering a substance, in particular one of a liquid, as a suspension or solution, or a powder containing a medicament, especially a topical pharmaceutical, a cleansing agent, or an irrigating agent, as a liquid, preferably combined with a cleansing agent, to the nasal airway of a subject. In particular, the present invention relates to the delivery of medicament to and the irrigation of the nasal mucosa, the anterior region of nasopharynx, the paranasal sinus ostia, the tubal ostia of the auditory tubes, the sinus tubes, the auditory tubes, the tympanic cavities and the paranasal sinuses.

BACKGROUND

Referring to FIG. 1, the nasal airway 1 comprises the two nasal cavities separated by the nasal septum, which airway 1 includes numerous ostia, such as the paranasal sinus ostia 3 and the tubal ostia 5, olfactory cells and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Worryingly, the incidence of such allergic and non-allergic inflammatory diseases is increasing. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Indeed, topical administration is advantageous in minimizing the possible side effects of systemic administration. Medicaments that are commonly topically delivered include decongestants, antihistamines, cromoglycates, steroids and antibiotics.

There are now an increasing number of adults and children who rely on pharmaceuticals to relieve symptoms associated with nasal conditions. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Aside from the delivery of medicaments, the irrigation of the nasal mucosa with liquids, in particular saline solutions, is commonly practiced to remove particles and secretions, as well as to improve the mucociliary activity of the nasal mucosa. These solutions can be used in combination with active pharmaceuticals.

Furthermore, medicaments are now increasingly systemically delivered through the nasal pathway, the nasal pathway offering a good administration route for the systemic delivery of pharmaceuticals, such as hormones, for example oxytocin, and antimigraine compositions, as the high blood flow and large surface area of the nasal mucosa advantageously provides for rapid systemic uptake.

A variety of delivery systems have been developed to deliver substances to the nasal airways of subjects.

Conventionally, spray bottles have been used to deliver a medicament-containing liquid or an irrigating liquid to the nasal airways of subjects. However, the distribution of the delivered substance, in particular to the posterior region of the nasal airway, is less than ideal, especially in the cases of moderate and severe nasal obstruction. This poor distribution is often further exacerbated by a subject inhaling through the nasal airway during delivery, as is often prescribed, in an attempt to deliver the substance to the posterior region of the nasal airway. Indeed, an amount of the substance can be drawn into the lungs or swallowed in each delivery, which could be problematic in paediatric subjects if the medicament is a potent pharmaceutical, such as a steroid, which has to be administered frequently. In addition, the spray is frequently directed against the nasal septum which can undesirably lead to localized deposition. Further, the mechanical action of the delivery mechanism of the spray bottles can cause irritation and bleeding.

GB-A-408856 discloses a delivery device, which, in one mode of use, allows for the inhalation of separate air flows entraining medicament into respective ones of the nasal cavities of a subject. This delivery device comprises a chamber containing a sponge saturated with medicament, a mouthpiece connected to the chamber and first and second nosepieces connected to the chamber. In one mode of use, the nosepieces are fitted into respective ones of the nostrils of a subject, and, on inhalation through the nosepieces, air flows entraining medicament are drawn into the lungs of the subject. In another mode of use, the mouthpiece is taken in the mouth of a subject, and, on inhalation through the mouthpiece, an air flow entraining medicament is drawn into the lungs of the subject.

WO-A-98/53869 discloses a delivery device for delivering a powder containing a medicament to the nasal mucosa in one of the nasal cavities of a subject. This device comprises a tubular section which contains a metered dose of powdered medicament. In use, the ends of the tubular section are respectively located in the nostril of one of the nasal cavities and the mouth of a subject, and on exhalation by the subject through his or her mouth the exhaled air entrains the powdered medicament and delivers the same into the one nasal cavity, with the exhaled air backflowing out of the one nostril around the tubular section. In one embodiment the tubular section includes a flexible portion upstream of the dose of powdered medicament. The provision of this flexible portion allows the subject to close the tubular section at a point upstream of the medicament, such that, on release of the closed flexible portion during exhalation, a short explosive air flow entraining medicament is delivered into the one nasal cavity. In another embodiment the end of the tubular section located in the nostril can be shaped to act to locate the tubular section in a position in the nostril which allows for the deposition of the powdered medicament on the nasal mucosa.

Whilst this delivery device is simple in construction, the operation of the device still does not provide for the effective delivery of substances, in particular one of a liquid or powder containing medicament, to the posterior region of the nasal airway, since medicament is delivered separately to each of the nasal cavities and the air flow into and out of each nasal cavity is through the same opening, namely the respective nostril, with the closed posterior region of the respective nasal cavity acting as a pressure reflecting surface which causes the exhaled air to backflow out of the one nostril before ever adequately reaching the posterior region of the respective nasal cavity. Further, in providing a short explosive burst of air flow into one of the nasal cavities, it is not possible to achieve a sustained and controlled bidirectional air flow through the nasal cavities which has been found necessary to deliver a substance effectively to the posterior region of the nasal airway.

For any substance to be delivered effectively to the nasal airway, it is highly desirable that the administration is efficient and simple. However, there can be problems in attempting to achieve this goal. In particular, the pathological changes observed with nasal inflammation make administration of substances, such as liquids or powders, tricky, particularly to the posterior region of the nasal airway and the posterior margins of the nasal structures. Indeed, as a consequence of the complex geometry of the narrow slit-like passages in the nasal airway, these passages become partially occluded when the nasal mucosa is inflamed and congested, making the distribution of topical pharmaceuticals to the nasal airway difficult.

SUMMARY OF THE INVENTION

It is thus an aim of the present invention to provide a delivery device for and a method of achieving a more optimally distributed deposition of a substance, especially topical pharmaceuticals, in the nasal airway, particularly the posterior region of the nasal airway, and in particular the anterior region of the nasopharynx where the adenoid and tubal ostia are located.

Accordingly, the present invention provides a delivery device for delivering a substance to the nasal airway of a subject, comprising: a closure unit for causing the closure of the oropharyngeal velum of the subject; and a delivery unit for delivering a gas flow entraining a substance to one of the nostrils of the subject at such a driving pressure as to flow around the posterior margin of the nasal septum and out of the other nostril of the subject, wherein the delivery unit comprises a nosepiece which includes an outlet through which the gas flow is in use delivered to the one nostril and a sealing member for sealing the one nostril to the outlet such as in use to prevent the escape of the gas flow through the one nostril.

In one embodiment the substance comprises a dry powder.

In another embodiment the substance comprises liquid droplets.

Preferably, the particle size distribution of the substance is principally in the range of about 1 to 10 μm.

In one embodiment the substance contains a medicament, particularly for the treatment of a nasal condition. In a preferred embodiment the particle size distribution of the substance can include a smaller fraction of larger particles, typically in the range of about 10 to 30 μm, and preferably in the range of about 20 to 30 μm.

In other embodiments the substance can be a cleansing agent, as a powder or liquid, for cleansing the nasal airway, or a liquid, which may preferably contain a cleansing agent, for irrigating the nasal airway. By way of example, the delivery device could be used to administer saline or other solutions to the nasal airway to remove particles and secretions, in particular from the posterior region of the nasal airway, which resulting solution could be analyzed for diagnostic or research purposes. In a preferred embodiment the particle size distribution of the cleansing or irrigating agents can include a fraction of larger particles, particularly in relation to the mechanical action of the particles.

The present invention also provides a method of delivering a substance to the nasal airway of a subject, comprising the steps of: sealing one of the nostrils of a subject to an outlet of a delivery unit such as to prevent the escape of a gas flow through the one nostril; closing the oropharyngeal velum of the subject; and delivering a gas flow entraining a substance through the outlet at such a pressure as to flow around the posterior margin of the nasal septum and out of the other nostril of the subject.

In one embodiment the closure of the velum is achieved directly by the use of an instrument for pressing against the velum to close the same or a bung for temporarily closing the opening behind the velum between the nasal airway and the oral cavity.

In a preferred embodiment the closure of the velum is achieved indirectly by the creation of a positive pressure in the oral cavity, or more correctly a positive pressure differential between the oral cavity and the nasal airway, such as achieved on exhalation.

Preferably, the velum is closed simultaneously with the onset of the delivery of the substance to the nasal airway.

In a preferred embodiment closure of the velum is achieved automatically by the subject exhaling against a flow resistor, which flow resistor may be operably connected to a tubular section held between the lips of the subject. The flow resistor can be configured to provide the required intra-oral positive pressure.

It has been established that flow rates of about 1 to 20 liters per minute, and particularly about 3 to 15 liters per minute, can be easily achieved by a subject and that and a fairly constant air flow can be maintained for up to 20 seconds depending on the flow rate. For some treatment regimes, it is important that a stable flow of relatively high flow rate be maintained for a period of a few seconds, preferably 3 to 10 seconds, in order to enable the substance to penetrate to the more remote parts of the nasal airway.

In one embodiment the air flow of exhalation by a subject is used to power a mechanism which disperses the substance into a volume of air and delivers that dispersed substance into the nasal airway.

Preferably, the mechanism is so arranged that the substance is delivered into the nasal airway after the velum has been closed or simultaneously with velum closure. In this respect, it will be understood that bidirectional flow through the nasal cavities is possible only when the velum is closed and that any substance delivered prior to closure of the velum would undesirably be delivered to the lower airway or the gut.

Preferably, the release of the substance into the nasal airway is triggered by the air flow created on exhalation.

In a preferred embodiment a pressure-sensitive valve is utilized to trigger release of the substance when a predetermined flow rate has been developed. It should be understood that control of the flow rate of the gas in which the substance is delivered is important, as this flow rate, along with the particle size distribution of the substance, are the significant factors determining the particle deposition efficiency.

In a preferred embodiment the pressure-sensitive valve is not opened until the subject has maintained a predetermined flow rate, and can be closed when the flow rate drops below the predetermined flow rate so as to stop the delivery of the substance.

In a preferred embodiment, where medicament is delivered in a driving gas, one or both of the timing and duration of the opening of the pressure-sensitive valve and the dose released are carefully controlled to ensure a standardized dosage.

In one embodiment, where the substance is released into a chamber and a gas flow, in one embodiment the exhalation flow, is provided to induce the mixing of a metered dose of the substance, the delivery of the gas flow can be prolonged to flush the nasal airway as this prolonged flushing does not effect the delivered dose. A mechanical device powered by a hand-chargeable spring, pressurized air or similar, may be used to provide the driving gas.

Regardless of the system employed, the flow characteristics can be optimized to improve the deposition of the substance and the comfort factor, such as to avoid an abrupt onset which is likely to induce withdrawal reflexes.

Preferably, a metered dose of the substance is dispensed into a delivery chamber by a dosing mechanism. This dosing mechanism can be constructed in such a way as to allow for a gradual release of the substance. This gradual release will better enable the substance to be entrained by the gas flow and thereby improve delivery to all ventilated parts of the nasal airway, in particular in the contralateral nasal cavity.

In a preferred embodiment the exhalation air flow developed by the subject, which closes the velum, provides the gas flow for entraining the substance and providing the bidirectional flow. This configuration is advantageous in that a separate driving gas flow need not be developed.

Preferably, the nosepiece is configured to extend about 1 cm into the one nasal cavity so as to expand the valve region, a region located about 2 to 3 cm within a nasal cavity which is usually the flow limiting region, and reduce the resistance which may be high in the case of nasal inflammation.

The shape of the nosepiece can be tailored to suit specific needs. For example, the internal shape of the nosepiece may be optimized to promote turbulence and achieve a more optimal dispersion of the substance.

The nosepiece may include a tight fitting nasal olive, which can aid the creation of a suitable physiological gas flow. The olive may be detachable such as to allow for other olives of the same or different dimensions to be fitted. In the case of severe nasal obstruction, a nasal olive can be introduced into the other nostril to reduce resistance and facilitate flow therethrough.

As mentioned above, a gas flow of at least 20 liters per minute can easily be achieved by the delivery device. By providing a sufficiently high gas flow, all parts, or at least a larger part, of the complex nasal airway can be penetrated by the substance. In one embodiment the delivery device can include an indicator for indicating the magnitude of the gas flow.

The dimensions of the posterior passage and opening behind the nasal septum are almost always larger than the opening in the flow resistor. Thus, it is only in very rare cases of complete occlusion of the outlet nostril that the pressure in the posterior region of the nasal airway will approach the positive pressure in the oral cavity and jeopardize the velum closure. In the case of severe obstruction, insertion of the nosepiece in the occluded nostril may reduce the resistance and allow successful flushing.

After having flushed the nasal airway in one direction, the same procedure can be repeated from the other nostril. In this way both nasal cavities are irrigated in both directions. This is a unique feature of this device. This embodiment secures an improved distribution of the substance to all parts of the nasal mucosa, and in particular to the posterior region which is difficult to access using current techniques.

In a preferred embodiment, where the substance is in solid form, such as a powder, then a filter can be employed if high humidity represents a problem for administration of the solid.

The substance can be a single compound or a mixture of compounds, which compounds can be in any suitable form, such as a powder form, a solution, or a suspension.

The substance can be any suitable substance for delivery to a human or in some cases an animal. The substance may be for delivery for action in any part of the nasal airway, or in any of the surrounding tissues or organs. Also, the substance may be for delivery for action in a region remote from the nasal airway.

Preferably, the substance is for delivery for subsequent action in any part of the nasal airway, or in any of the surrounding tissues or organs.

The substance may have a beneficial medical effect, which can include a diagnostic effect, a therapeutic effect, a prophylactic effect, and a cleansing effect such as the removal of particles, crusts, secretions, debris, etc. Preferably, the substance has a therapeutic effect.

Preferably, the substance is a pharmaceutical. The pharmaceutical can be admixed with any suitable carrier, diluent, excipient or adjuvant.

Preferably, the pharmaceutical is for the treatment of any one or more of the abovementioned conditions. By way of example, the pharmaceutical may be for the treatment of any allergic and non-allergic inflammatory disease.

Typical pharmaceuticals for administration include, but are not limited to, steroids, anti-histamines, cromoglycates, anti-allergic pharmaceuticals, anti-inflammatory pharmaceuticals, anti-leucotriens, lactation promoters such as oxytocin, and antimigraine pharmaceuticals.

By achieving a more optimal delivery, the delivery device of the present invention improves the effect of topical pharmaceuticals in the treatment of upper airway pathologies, such as hypertrophic adenoids and chronic secretory otitis media.

Aside from pharmaceuticals, the device can also be used to irrigate or cleanse the nasal airway with saline or other solutions, preferably containing oils or herbs.

The device of the present invention can be tailored to suit particular needs. For example, balloons or pop-up figures can easily be integrated to provide a semiquantitaive indication of the flow rate and to improve the acceptability and ease of administration in small children.

Only in the rare circumstances when the nasal resistance is too high to achieve a gas flow through the nasal airway, even after attempting to expand the nasal cavities, would insufflation be jeopardized. In those cases, pre-treatment with decongestants may be necessary.

The delivery device may also be used as a nasal lavage means in the collection of mediators and cells that originate from the nasal mucosa for, for example, diagnostic analysis or research purposes. In this respect, the mediators and cells can be expelled into a suitable collecting vessel after the nasal airway has been exposed to a suitable solution, such as a saline solution, for a sufficient period of time to ensure sufficient transfer of the mediators and cells into the solution. This use of the device may require the use of a gas flow separate to the exhaled air flow as the flow used to flush the nasal airway. For this lavage purpose, use of the exhaled air may not be possible as the lower airways may contain mediators, secretions and cells originating from the lower airways which would contaminate the nasal sample. For this particular use, and as indicated, the fluid escaping from the outlet nostril may be collected in a vessel. Alternatively, the fluid escaping from the outlet nostril may be absorbed onto a filter for direct or delayed analysis. Indeed, such filters and the like may even yield an almost immediate detection result of certain organisms, such as bacteria, viruses or mediators.

The delivery device of the present invention is advantageous for a number of reasons.

Notably, the delivery device provides a very simple and efficient means of delivering substances, such as pharmaceuticals, saline solutions, etc, into the nasal airway. In this respect, the device utilizes very simple technology with few movable parts, making the device relatively inexpensive to mass produce. In addition, the device of the present invention can be made in a disposable form, thus avoiding the need for the delivered substance to include any preservatives.

The present invention also eliminates the need for the subsequent flushing or spraying methods that are associated with some of the prior art devices. However, for some applications it may still be desirable to perform a subsequent flushing or spraying operation.

The delivery device of the present invention is advantageous as, in use, the tight seal between the nosepiece and the one nostril ensures a prolonged penetration of the complex nasal airway, a bidirectional gas flow through the nasal cavities and deposition of the substance in the contralateral nasal passage.

In accordance with the present invention, closure of the velum will normally be maintained. The delivered gas flow enters one nasal cavity, passes beyond the posterior margin of the nasal septum, making a 180 degree turn behind the posterior margin of the nasal septum, and passes out the other nasal cavity. This redirection of the gas flow results in a better deposition of substance, notably pharmaceuticals, to the posterior regions of the nasal turbinates and the nasal mucosa.

In addition, the bidirectional deposition of substances, typically pharmaceuticals, and irrigation will also better reach all sinus ostia due to the anatomic locations and orientation of the sinus ostia, which can improve sinus ventilation and drainage which is essential to treat sinusitis and frequently accompanies inflammation of the nasal mucosa. In this respect, the ostia and tubes to the ethmoidal and sphenoidal sinuses are located in the posterior region of the nasal airway and the uncinate projections covering the infundibulum, housing the maxillary, frontal and anterior ethmoid ostia, are tilted backwards. Furthermore, the driving positive pressure used will increase the deposition of pharmaceuticals at the sinus ostia, the sinus tubes leading into the sinuses and even in the sinuses themselves.

In addition, the 180 degree redirection of the flow behind the nasal septum particularly increases the deposition of substance on the roof of the nasopharynx where the adenoid is located and in proximity to the location of the tubal ostia to the auditory tubes connecting the nasopharynx and the middle ears. By way of example, steroids have been shown to reduce the size of hypertrophic adenoids which are commonly found in paediatric subjects and can have a positive effect on secretory otitis media. Deposition of topical decongestants closer to the tubal ostia may also more efficiently decongest the auditory tubes and relieve the negative pressure in the middle ears which accompanies rhinitis and predisposes paediatric subjects to secretory otitis media and the consequential reduced hearing. Surgery for enlarged adenoids is frequently performed in children and the improved medical therapy of the present invention should reduce the necessity for surgery.

A further advantage is that possible surplus substance, that is, substance which is not deposited, will be expelled out of the contralateral nostril, where it may be collected, if desired, and consequently not continue to the oral cavity and down into the gut as is the case with many other delivery techniques. In this way, the discomfort, and more importantly, the undesirable systemic exposure to the substance, where the substance is a medicament, will be reduced.

Also, with the present invention, irrigation by saline or other solutions can be performed more efficiently and with less spill and discomfort than the current techniques used for irrigation and flushing of the nasal airway.

Further, the present invention provides for simple and comfortable irrigation of the nasal mucosa with solutions, such as saline solutions, and other oils to remove secretions from the nasal mucosa and promote mucociliary function.

Still further, the present invention provides a simple and effective means for the lavage of the nasal mucosa, such as to collect and diagnose mucosal entities, such as bacteria, viruses, cell components and inflammatory mediators.

Still yet further, the exposure of the nasal mucosa to a positive pressure, particularly a dynamic positive pressure, will open the narrow, and sometimes occluded, parts of the nasal passages, rather than cause a dynamic collapse which may happen during sniffing and inhalation. The dynamic positive pressure is at least 5 cm $H_2O$, preferably at least 50 cm $H_2O$, more preferably at least 100 cm $H_2O$, still more preferably at least 200 cm $H_2O$, yet more preferably 400 cm $H_2O$ and still yet more preferably 500 cm $H_2O$. The dynamic positive pressure achieved by the present invention can be contrasted with the static pressure provided by the Valsalva procedure where there is no flow through the nasal airway.

In addition, the use of warm and humid air as the gas flow is likely to be better tolerated and cause less irritation than room air or outdoor air, especially in cold climates.

Where the substance is a dry powder, then the humidity of the exhaled air may, in some instances, cause agglomeration of the powder. Naturally, this will depend on the properties of the powder and the construction of the device, in particular the dispersion chamber. In order to alleviate this specific problem, the surface properties of the powder could be modified, or the device could include a moisture-absorbing element, typically containing a desiccant such as silica, disposed upstream of the dispersion chamber. In a preferred embodiment the moisture-absorbing element could be provided as a filter which acts as the flow resistor.

In a preferred embodiment, in order to ensure that agglomeration of powder would not impede the use of direct insufflation of warm, humid exhaled air, the delivery device comprises transfer means which creates a gas flow of such as atmospheric air, as the delivery flow to the nasal airway. Such transfer mean, which could be mechanical in nature, utilises the energy of the exhaled air to drive the atmospheric room air at the required flow rate, if necessary, to disperse the substance in the delivered air flow. In this embodiment agglomeration will be prevented or at least reduced to the same level as currently exhibited by dry powder inhalers.

If desired, the distribution of the substance delivered to the nasal airway could be studied using standard techniques. By way of example, use could be made of acoustic rhinometry or coloured fluids. The distribution of the delivered substance could even be determined by video endoscopy. In addition, or in the alternative, distribution studies could also be performed by using appropriate radioactive materials and following the passage in the nasal cavities. The results of these studies could be used to optimise the flow rate, the shape or dimension of the device, in particular nosepiece geometry, and the particle size distribution of the substance. The results of these studies could even be used to optimize subject acceptance.

As already indicated, the delivery device may include a balloon or a similar pop-up device for indicating that the desired positive pressure has been attained, which balloon or pop-up device may improve the compliance in small children who are reluctant to use the device.

Alternatively, for particularly young children, the entraining gas flow can be provided by the exhalation air flow of another person, such as a parent, or even by the use of a pump or the like, while the child creates the required positive pressure in the oral cavity by inflating a balloon or pop-up device.

BRIEF DESCRIPTION OF THE DRAWINGS

Preferred embodiments of the present invention will now be described hereinbelow by way of example only with reference to the accompanying drawings, in which:

FIG. 1 schematically illustrates the anatomy of the upper respiratory tract of a human subject;

FIG. 2 schematically illustrates a delivery device in accordance with a first embodiment of the present invention;

FIG. 3 schematically illustrates a delivery device in accordance with a second embodiment of the present invention;

FIG. 4 schematically illustrates a delivery device in accordance with a third embodiment of the present invention;

FIG. 5 schematically illustrates a modified delivery unit for the above-described first to third embodiments of the present invention;

FIG. 6 schematically illustrates a delivery device in accordance with a fourth embodiment of the present invention;

FIG. 7 schematically illustrates a delivery device in accordance with a fifth embodiment of the present invention;

FIG. 8 schematically illustrates a delivery device in accordance with a sixth embodiment of the present invention; and FIG. 9 schematically illustrates a delivery device in accordance with a seventh embodiment of the present invention.

DETAILED DESCRIPTION

FIG. 2 illustrates a delivery device in accordance with a first embodiment of the present invention.

The delivery device comprises an oral exhalation unit 20 and a substance delivery unit 22. In this embodiment the oral exhalation unit 20 and the delivery unit 22 are provided as separate components, but alternatively could be detachably coupled, for example by means of Velcro™ fasteners, connected, for example by means of screws and/or rivets, or even integrally formed.

The oral exhalation unit 20 comprises a tubular section 24 and a mouthpiece 26 attached to one end of the tubular section 24. The mouthpiece 26, which in use is gripped in the lips of a user, is formed separately of the tubular section 24 to allow for replacement, but could alternatively be integrally formed. In this embodiment the mouthpiece 26 is a snap fit on the tubular section 24, but could equally be a screw fit. The tubular section 24 includes a flow resistor 28, in this embodiment a fixed baffle plate, configured to provide a sufficient resistance to exhalation therethrough by a subject as to cause the generation of a positive pressure in the oral cavity of the subject and the closure of the velum on exhalation by the subject. In alternative embodiments the flow resistor 28 could be a movable member, such as a biased flap, a resilient membrane or a damped wheel.

The delivery unit 22 comprises a nosepiece 30, in this embodiment formed of a resilient material such as a polymeric material, for providing a tight sealing fit in one of the nostrils of the subject, a medicament supply unit 32 for supplying a gas flow entraining medicament at a predetermined pressure sufficient to open a flow path beyond the posterior margin of the nasal septum when delivered into one of the nasal cavities of the subject, and a tubular section 34 coupling the nosepiece 30 and the medicament supply unit 32. In a preferred embodiment the nosepiece 30 can include an external olive or be shaped to cause the anterior region of the nasal cavity into which the nosepiece 30 is inserted to be enlarged. In a particularly preferred embodiment the nosepiece 30 can be shaped, for example by including swirl-inducing projections, to provide the exiting gas flow with an optimal flow pattern and particle size distribution. The nosepiece 30 is formed separately of the tubular section 34 to allow for replacement, but could alternatively be integrally formed. In this embodiment the nosepiece 30 is a snap fit on the tubular section 34, but could equally be a screw fit. The medicament supply unit 32 can comprise an aerosol spray generator for generating an aerosol spray of liquid droplets containing medicament, such as provided by a pressurized metered dose inhaler, or a pressurized gas source for entraining a metered dose of a dry powder containing medicament loaded thereinto, which powder could alternatively be loaded into a compartment in the tubular section 34.

In use, a subject grips the mouthpiece 26 in his or her lips and fits the nosepiece 30 into one of his or her nostrils. The subject then exhales through the mouthpiece 26, the flow of which exhaled air is resisted by the flow resistor 28 in the tubular section 24 such as to develop a positive pressure in the oral cavity of the subject, with the positive pressure being such as to develop a pressure differential across the velum sufficient to cause closure of the velum of the subject. The applicant has established that a positive pressure differential between the oral cavity and the nasal airway of about 5 cm H20 is required to maintain the velum in the closed position. The applicant has further established that a subject should be able to maintain a flow rate of about 3 to 30 liters per minute for about 1 to 20 seconds, with flow rates of about 10 to 20 liters per minute and delivery times of about 2 to 5 seconds being considered as optimal. After closure of the velum, the medicament supply unit 32 is then actuated to deliver a gas flow entraining medicament through the nosepiece 30 and into the nasal airway of the subject. As mentioned above, this gas flow is at such a pressure as to open a communication path beyond the posterior margin of the nasal septum such that the gas flow flows through the one nasal cavity, around the posterior margin of the nasal septum, in effect being redirected through an angle of 180 degrees, and out of the other nasal cavity. Again, as already described, this bidirectional flow provides for a much enhanced deposition of the medicament in the posterior region of the nasal airway.

In one modification, the medicament supply unit 32 can be omitted from the delivery unit 22, and instead a metered dose of dry powder loaded into a compartment in the tubular section 34, with the delivery air flow being provided by another person, such as the parent of a paediatric subject, blowing into the distal end of the tubular section 34.

Figure 3:
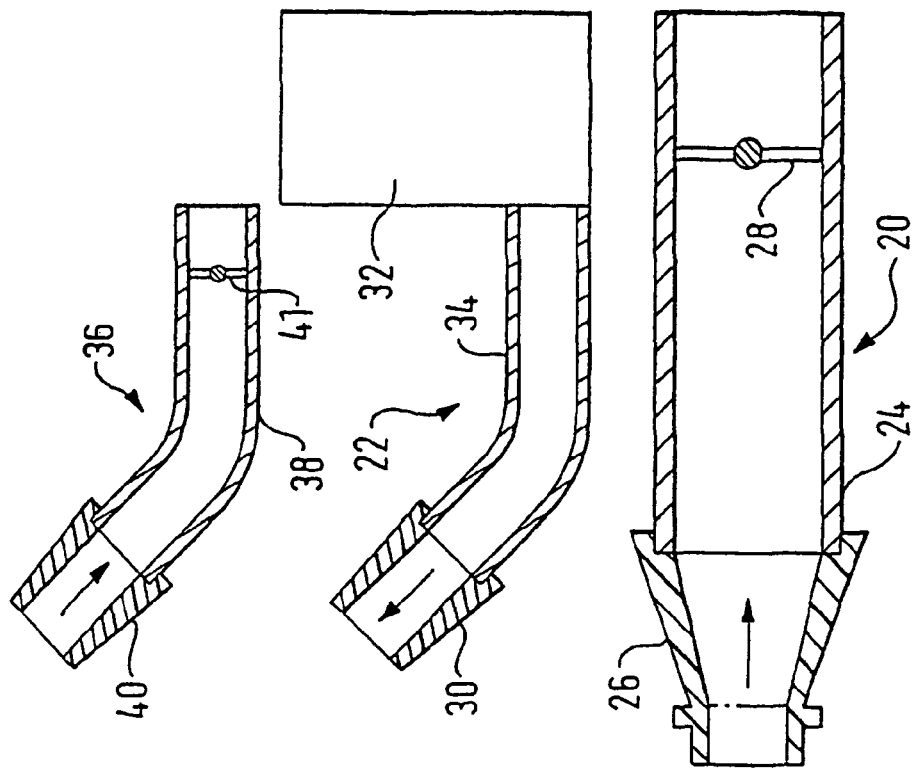
Figure 2:
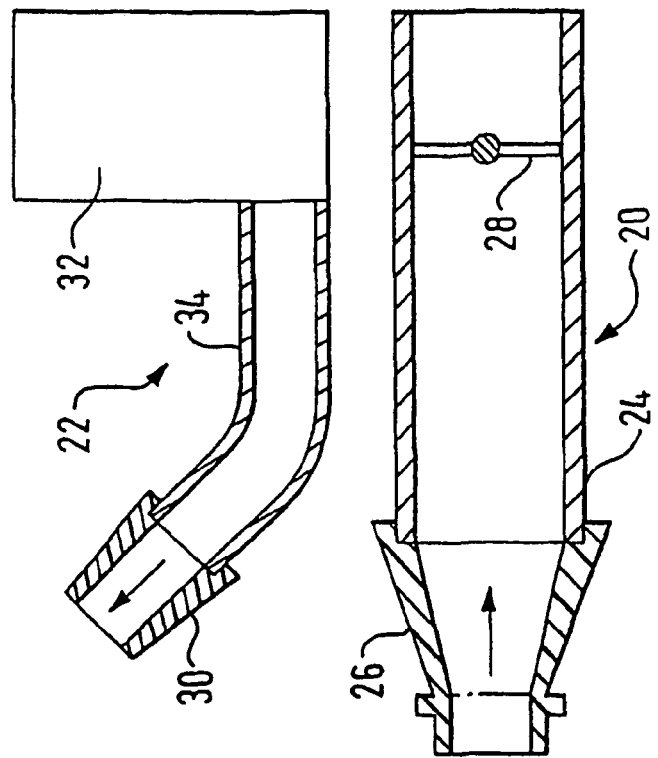

FIG. 3 illustrates a delivery device in accordance with a second embodiment of the present invention.

The delivery device comprises the oral exhalation unit 20 and the delivery unit 22 of the above-described first embodiment, and an outlet unit 36 for fitting to the other nostril of a subject to which the delivery unit 22 is fitted.

The outlet unit 36 comprises a tubular section 38 and a nosepiece 40, in this embodiment formed of a resilient material such as a polymeric material, attached to one end of the tubular section 38 for providing a tight sealing fit in the other nostril of the subject. The nosepiece 40 is formed separately of the tubular section 38 to allow for replacement, but could alternatively be integrally formed. In this embodiment the nosepiece 40 is a snap fit on the tubular section 38, but could equally be a screw fit. As with the nosepiece 30 of the delivery unit 22, in a preferred embodiment the nosepiece 40 can include an external olive or be shaped to cause the anterior region of the other nasal cavity into which the nosepiece 40 is inserted to be enlarged. The tubular section 38 includes a flow resistor 41, in this embodiment a baffle plate, configured to provide a sufficient flow resistance to an exhalation flow therethrough as to cause the generation of a dynamic positive pressure in the nasal airway. In a preferred embodiment the flow resistor 41 is adjustable to allow for adjustment of the level of the resistance and hence provide control of the dynamic pressure in the nasal airway. In alternative embodiments the flow resistor 41 could be a movable member, such as a biased flap, a resilient membrane or a damped wheel.

In a preferred embodiment the outlet unit 36 includes an indicator for providing at least one of a visual or audible signal on achieving a predetermined positive pressure upstream thereof, that is, in the nasal airway. Preferably, the indicator comprises a whistle. In this way, the subject is provided with positive feedback of proper use of the device.

Use of the delivery device of this embodiment is the same as for the above-described first embodiment. However, as mentioned above, by the provision of the flow resistor 41 in the outlet unit 36 downstream of the outlet nostril of the subject, a positive dynamic pressure is maintained in the nasal airway. This positive pressure advantageously acts to dilate the various ostia in the nasal airway, such as the sinus ostia and the tubal ostia, and the associated tubes, namely the sinus tubes and the auditory tubes, so as to promote the delivery of medicament thereto. Further, this positive pressure acts to improve deposition on the adenoid which can often obstruct the tubal ostia, the middle meatus which is a common location of nasal polyps, and the cleft to the olfactory cells.

FIG. 4 illustrates a delivery device in accordance with a third embodiment of the present invention.

The delivery device is very similar to that of the delivery device of the above-described second embodiment, and thus, in order to avoid unnecessary duplication of description, only the differences will be described in detail, with like parts being designated by like reference signs. This delivery device differs only in further comprising a pressure sensor 43, in this embodiment a pressure-sensitive spring or membrane, located in the tubular section 34 of the delivery unit 22 downstream of the medicament supply unit 32, and a control unit 44 coupled to the sensor 43 and the medicament supply unit 32.

The control unit 44 is configured to control the flow rate of the delivery gas supplied by the medicament supply unit 32 in order to optimize the particle deposition efficiency in the nasal airway regardless of the degree of nasal congestion. As mentioned hereinabove, by maintaining an optimum flow rate in the nasal airway, the deposition efficiency of the medicament-containing particles is increased, referred to as the particle deposition efficiency. If, ordinarily, a flow rate of about 15 liters per minute is required to maximize the particle deposition efficiency, then in a congested nasal airway a lower flow rate, possibly 10 liters per minute, would be required and in an open nasal airway a higher flow rate, possibly 20 liters per minute, would be required.

Operation of this delivery device is otherwise the same as that of the above-described second embodiment.

FIG. 5 illustrates a modified oral exhalation unit 20 for the delivery devices of the above-described embodiments.

This modified oral exhalation unit 20 differs in that the tubular section 24 includes a lateral opening 45 upstream of the flow resistor 28 and in further comprising, as an indicator, an inflatable figure 46 connected to the lateral opening 45, which figure 46 when inflated assumes a prominent position in the field of vision of the subject. In FIG. 4, the figure 46 is shown inflated. By providing such a display feature, subject compliance, particularly in paediatric subjects, should be improved. The oral exhalation unit 20 further comprises an inflation line 48 connected to the figure 46 which allows the figure 46 to be further inflated by another person, typically the parent of a paediatric subject, or a pump. In an alternative embodiment, instead of being inflatable, the figure 46 could be of any kind which is brought into a prominent position on exhalation by the subject, typically a mechanically or electrically-operated figure. In a preferred embodiment the figure 46 can be configured so as to be inflated on the subject achieving an optimum exhalation flow rate. In this way, the figure 46 acts as an indicator.

Use of the delivery device of this embodiment is the same as that of the abovedescribed first embodiment. However, on exhaling through the mouthpiece 26, the developed pressure causes the figure 46 to be inflated and assume a prominent position in the field of vision of the subject. This appearance of the figure 46 is particularly appealing for paediatric subjects as the fun element of inflating the figure 46 can alleviate any unnecessary anxiety.

Figure 6:
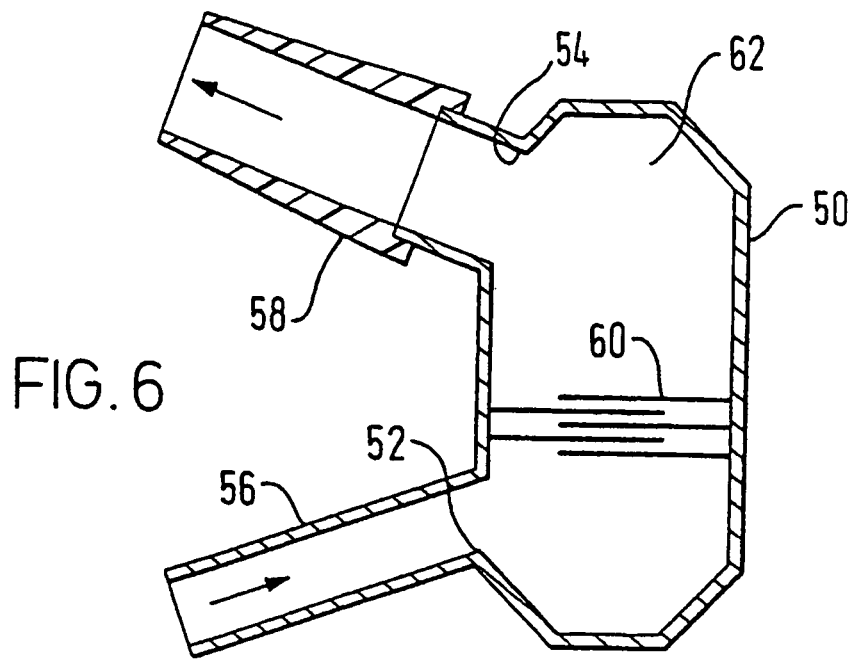

FIG. 6 illustrates a delivery device in accordance with a fourth embodiment of the present invention.

The delivery device comprises a chamber 50 which includes an inlet 52 and an outlet 54, a mouthpiece 56 connected to the inlet 52 and a nosepiece 58 connected to the outlet 54. The nosepiece 58 is configured to provide a tight sealing fit in one of the nostrils of a subject. The chamber 50 includes a flow resistor 60, in this embodiment a plurality of baffle plates, and a medicament-receiving compartment 62 downstream of the flow resistor 60 for containing a metered dose of a dry powder containing medicament to be delivered to the nasal airway of a subject. In this embodiment the nosepiece 58 is formed of a resilient material such as a polymeric material. In a preferred embodiment the chamber 50 may include a desiccant. In a preferred embodiment the flow resistor 60 can be provided by a moisture-absorbing filter.

In use, a subject grips the mouthpiece 56 in his or her lips and fits the nosepiece 58 into one of his or her nostrils. The subject then exhales through the mouthpiece 56, the flow of which exhaled air is resisted by the flow resistor 60 in the chamber 50 and the resistance of the nasal airway such as to develop a positive pressure in the oral cavity of the subject sufficient to cause closure of the velum. The exhaled air, after passing the flow resistor 60, then entrains the powdered medicament in the medicament receiving compartment 62, and this air flow entraining medicament then passes through the nosepiece 58 into the nasal airway of the subject. The exhaled air entering the nasal airway is at a pressure sufficient to open a communication path beyond the posterior margin of the nasal septum such that the air flow flows through the one nasal cavity, around the posterior margin of the nasal septum, in effect being redirected through an angle of 180 degrees, and out of the other nasal cavity. Again, as already described, this bidirectional flow provides for a much enhanced deposition of the medicament in the posterior margin of the nasal airway.

In a preferred embodiment the delivery device includes a pressure-triggered valve, preferably located in the mouthpiece 56, which is configured to open only when a predetermined positive pressure has been developed by the exhalation of the subject, typically at a positive pressure of about 10 cm $H_2O$. This configuration advantageously avoids the possibility of medicament being delivered to the nasal airway with the velum in the open position and thereby reduces the risk of undesirably depositing medicament outside the nasal airway.

In another preferred embodiment, similarly to third-described embodiment, the delivery device can include an outlet unit for providing a flow resistor downstream of the other nostril of the subject such as to maintain a positive dynamic pressure in the nasal airway.

Figure 7:
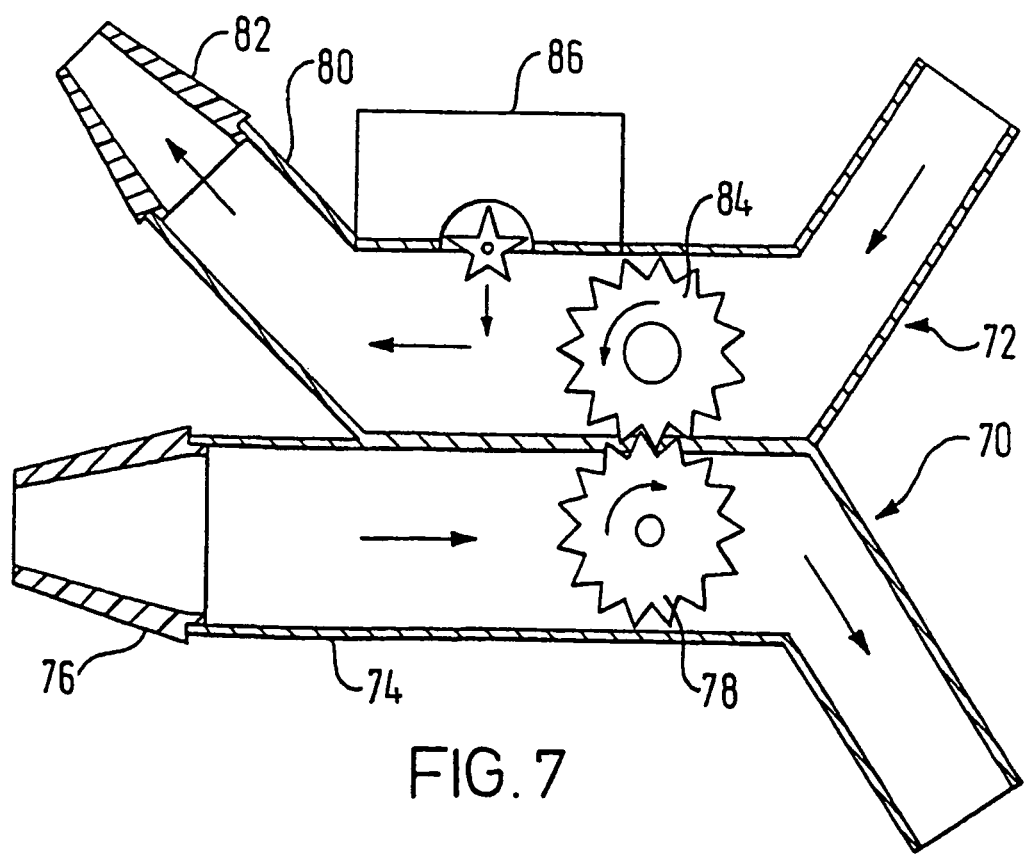

FIG. 7 illustrates a delivery device in accordance with a fifth embodiment of the present invention.

The delivery device comprises an oral exhalation unit 70 through which a subject exhales to close his or her velum and a medicament delivery unit 72 for supplying an air flow entraining medicament to the nasal airway of the subject.

The oral exhalation unit 70 comprises a tubular section 74 and a mouthpiece 76 attached to one end of the tubular section 74. The mouthpiece 76, which is gripped in the lips of the subject, is formed separately of the tubular section 74 to allow for replacement, but could alternatively be integrally formed therewith. In this embodiment the mouthpiece 76 is a snap fit on the tubular section 74, but could equally be a screw fit. The tubular section 74 includes a flow resistor 78, in this embodiment a gearwheel, configured to rotate on exhalation by the subject and yet provide sufficient resistance to the exhalation flow as to cause the generation of a positive pressure in the oral cavity of the subject sufficient to maintain the required positive pressure differential between the oral cavity and the nasal airway and thereby maintain the velum in the closed position.

The delivery unit 72 comprises a tubular section 80 and a nosepiece 82, in this embodiment formed of a resilient material such as a polymeric material, for providing a tight sealing fit in one of the nostrils of the subject, attached to one end of the tubular section 80. The nosepiece 82 is formed separately of the tubular section 80 to allow for replacement, but could alternatively be integrally formed therewith. In this embodiment the nosepiece 82 is a snap fit on the tubular section 80, but could equally be a screw fit. In a preferred embodiment the nosepiece 82 can include an external olive or be shaped to cause the anterior region of the nasal cavity, into which the nosepiece 82 is inserted, to be enlarged. In a particularly preferred embodiment the nosepiece 82 can be shaped, for example by including swirl-inducing projections, to provide the exiting air flow with an optimal flow pattern and particle size distribution. The tubular section 80 includes an impeller 84 coupled to the gearwheel 78 in the tubular section 74 of the oral exhalation unit 70, such as to be rotated on rotation of the gearwheel 78 to draw air into the tubular section 80 and provide an air flow therethrough at a pressure sufficient to open the flow path beyond the posterior margin of the nasal septum when delivered into one of the nasal cavities of the subject.

The delivery unit 72 further comprises a dispensing unit 86 for dispensing a metered dose of a dry powder containing medicament to the tubular section 80 upstream of the impeller 84. In this embodiment the dispensing unit 86 is manually actuated to supply a metered dose of dry powder containing medicament into the tubular section 80, but could alternatively be configured to the driven by the gearwheel 78 so as to avoid the need for any manual intervention on the part of the subject.

In use, a subject grips the mouthpiece 76 in his or her lips and fits the nosepiece 82 into one of his or her nostrils. The subject then exhales through the mouthpiece 76, the flow of which exhaled air is resisted by the gearwheel 78 such as to develop a positive pressure in the oral cavity of the subject sufficient to cause the velum of the subject to close. The exhaled air causes rotation of the gearwheel 78 which in turn causes rotation of the impeller 84, and the rotation of the impeller 84 develops an air flow through the tubular section 80 which entrains the metered dose of dry powder containing medicament and delivers the same through the nosepiece 82 to the nasal airway of the subject. As mentioned above, this air flow is at a pressure sufficient to open a communication path beyond the posterior margin of the nasal septum such that the air flow flows through the one nasal cavity, around the posterior margin of the nasal septum, in effect being redirected through an angle of 180 degrees, and out of the other nasal cavity. Again, as already described, this bidirectional flow provides for a much enhanced deposition of the medicament in the posterior region of the nasal cavity.

In a preferred embodiment the gearwheel 78 is configured such that rotation thereof is prevented until a predetermined flow rate has been developed which is sufficient to ensure that the entraining gas flow developed by the impeller 84 is optimal. This configuration advantageously ensures an optimal particle deposition efficiency and avoids the possibility of medicament being delivered to the nasal airway with the velum in the open position so as to reduce the risk of undesirably depositing medicament outside the nasal airway.

FIG. 8 illustrates a delivery device in accordance with a sixth embodiment of the present invention.

The delivery device comprises a housing 90 for housing a blister pack element 92 which includes a plurality of blisters 94 therein, each containing powder containing medicament, and a tubular section 96 in communication with one of the blisters 94 when open, one end of which tubular section 96 provides a mouthpiece 98 which in use is gripped in the lips of a subject. The tubular section 96 includes an element 100 movably disposed therein between a first, normally closed position and a second, open position. In this embodiment the element 100 comprises a propeller or the like rotatably mounted on a threaded shaft and normally biased to the closed position by a compression spring. The element 100 is configured both to function as a flow resistor and a valve. In this embodiment the element 100 is configured to move to the medicament-releasing open position by rotation along the threaded shaft against the bias of the compression spring, with the powder being entrainable by an air flow only when the exhalation flow exceeds a predetermined flow rate. The flow rate, preferably in the range of about 5 to 20 liters per minute, at which the powder containing medicament is entrained by the air flow is a function, in inverse relation, to the driving pressure which is itself a function of the nasal resistance as described hereinabove. As will be understood, this configuration advantageously provides for an optimal particle deposition efficiency in releasing the powder containing medicament at the optimal flow rate, and avoids the possibility of medicament being delivered to the nasal airway with the velum in the open position.

The delivery device further comprises a nosepiece 102, in this embodiment formed of a resilient material such as a polymeric material, for providing a tight sealing fit in one of the nostrils of the subject attached to the other end of the tubular section 96 downstream of the element 100. The nosepiece 102 is formed separately of the tubular section 96 to allow for replacement, but could alternatively be integrally formed therewith. In this embodiment the nosepiece 102 is a snap fit on the tubular section 96, but could equally be a screw fit. In a preferred embodiment the nosepiece 102 can include an external olive or be shaped to cause the anterior region of the nasal cavity into which the nosepiece 102 is inserted to be enlarged. In a particularly preferred embodiment the nosepiece 102 can be shaped, for example by including swirl-inducing projections, to provide the exiting air flow with an optimal flow pattern and particle size distribution.

The delivery device further comprises a blister opening mechanism 104 for opening the blister 94 in communication with the tubular section 96. In this embodiment the blister opening mechanism 104 is manually operated by the subject prior to delivery.

In use, a subject grips the mouthpiece 98 in his or her lips and fits the nosepiece 102 into one of his or her nostrils. The subject then exhales through the mouthpiece 98, the flow of which exhaled air is resisted by the element 100 until a predetermined flow rate has been achieved. Once this predetermined flow rate has been achieved, at which flow rate the velum is in the closed position, the element 100 is in the open position and the exhaled air flow entrains the powdered medicament in the blister 94 and delivers the same through the nosepiece 102 to the nasal airway. The driving pressure of this air flow is at a level sufficient to maintain a communication path beyond the posterior margin of the nasal septum such that the air flow flows through the one nasal cavity, around the posterior margin of the nasal septum, in effect being redirected through an angle of 180 degrees, and out of the other nasal cavity. Again, as already described, this bidirectional flow provides for a much enhanced deposition of the medicament in the posterior margin of the nasal cavity.

In a preferred embodiment the delivery device includes a blister pack advancement mechanism, operated by movement of the mouthpiece 98, for rotating the blister pack element 92 such that another unused blister 94 is located at the delivery position. In a particularly preferred embodiment the blister pack advancement mechanism can be coupled to the blister opening mechanism 104 such as automatically to open the blister 94, and thereby avoid the need for any further intervention by the subject.

In one modification, similarly to the above-described modification of the first embodiment as illustrated in FIG. 3, the delivery device can include an outlet unit for providing a flow resistor downstream of the other nostril of the subject such as to maintain a positive dynamic pressure in the nasal airway.

In another modification, the blister pack element 92 can be omitted and the housing 90 instead provided with a chamber which is in communication with the tubular section 96 and into which a metered dose of dry powder containing medicament can be loaded. With this configuration, the powder in the chamber is entrained on the element 100 being driven to the second position and the blister pack advancement mechanism is configured to meter a dose of powder containing medicament into the chamber on operation thereof.

As will be understood, in essence, the present invention can be broadly based on any dry powder inhaler, such as the Turbuhaler™ as manufactured by AstraZeneca PLC, the Accuhaler™ as manufactured by Glaxo PLC or the Twisthaler™ as manufactured by Schering AG, where the usual mouthpiece is replaced by a nosepiece and a mouthpiece is provided in communication with the air inlet of the inhaler such as to utilize the air exhaled by a subject as the entraining delivery air.

FIG. 9 illustrates a delivery device in accordance with a seventh embodiment of the present invention.

The delivery device comprises a housing 110 and a tubular section 112 extending through the housing 110, one end of which provides a mouthpiece 114 which in use is gripped in the lips of a subject.

The tubular section 112 includes an element 116 movably disposed therein between a first, normally closed position and a second, trigger position. In this embodiment the element 116 comprises a propeller or the like rotatably mounted on a threaded shaft and normally biased to the closed position by a compression spring. The element 116 is configured to function as a flow resistor, a valve and a trigger for the delivery of an aerosol spray into the tubular section 112 as will be described in detail hereinbelow. In this embodiment the element 116 is configured to move to the medicament-releasing open position, by rotation along the threaded shaft against the bias of the compression spring, only when the exhalation flow exceeds a predetermined flow rate. The flow rate at which the medicament is released, preferably in the range of about 5 to 20 liters per minute, is a function, in inverse relation, to the driving pressure which is itself a function of the nasal resistance as described hereinabove. As will be understood, this configuration advantageously provides for an optimal particle deposition efficiency in releasing the medicament at the optimal flow rate, and avoids the possibility of medicament being delivered to the nasal airway with the velum in the open position.

The tubular section 112 further includes a nozzle block 117 for providing an aerosol spray through the tubular section 112 along the longitudinal axis thereof. As will be described in detail hereinbelow, the nozzle block 117 receives the valve stem 122 of an aerosol canister 120.

The delivery device further comprises a known aerosol canister 120 used to deliver metered volumes of a propellant, preferably a hydrofluoroalkane (HFA) propellant or the like, containing medicament, either as a suspension or as a solution. The aerosol canister 120 comprises a main body 121 which contains a volume of propellant under pressure containing medicament, a valve stem 122 through which the propellant containing medicament is in use delivered on relative movement of the main body 121 and the valve stem 122, and a metering valve 124 for metering a predetermined volume of propellant containing medicament to the valve stem 122 on movement thereof.

The delivery device further comprises a trigger mechanism 126 for relatively moving the main body 121 and the valve stem 122 of the aerosol canister 120 to effect the delivery of a metered volume of propellant containing medicament through the nozzle block 117. In this embodiment the trigger mechanism 126 comprises a resilient element 128 for loading the main body 121 with an actuation force, and a lever assembly 130 coupled to the movable element 116 to cause the release of the actuation force provided by the resilient element 128 on movement of the movable element 116 from the closed position to the trigger position.

The delivery device further comprises a nosepiece 132, in this embodiment formed of a resilient material such as a polymeric material, for providing a tight sealing fit in one of the nostrils of the subject, attached to the other end of the tubular section 112 downstream of the movable element 116. The nosepiece 132 is formed separately of the tubular section 112 to allow for replacement, but could alternatively be integrally formed therewith. In this embodiment the nosepiece 132 is a snap fit on the tubular section 112, but could equally be a screw fit. In a preferred embodiment the nosepiece 132 can include an external olive or be shaped to cause the anterior region of the nasal cavity into which the nosepiece 132 is inserted to be enlarged. In a particularly preferred embodiment the nosepiece 132 can be shaped, for example by including swirl-inducing projections, to provide the exiting air flow with an optimal flow pattern and particle size distribution.

In use, a subject primes the trigger mechanism 126, grips the mouthpiece 114 in his or her lips and fits the nosepiece 132 into one of his or her nostrils. The subject then exhales through the mouthpiece 114, the flow of which exhaled air is resisted by the movable element 116 until a predetermined flow rate has been achieved. Once this predetermined flow rate has been achieved, at which flow rate the velum is in the closed position, the movable element 116 is in the open position, triggering the movement of the lever assembly 130 and hence the relative movement of the main body 121 and the valve stem 122 of the canister 120 to deliver a metered volume of propellant containing medicament to the nozzle block 117 to generate an aerosol spray of liquid droplets containing medicament through the nosepiece 132 to the nasal airway. This aerosol flow is at a pressure sufficient to maintain a communication path beyond the posterior margin of the nasal septum such that the flow flows through the one nasal cavity, around the posterior margin of the nasal septum, in effect being redirected through an angle of 180 degrees, and out of the other nasal cavity. Again, as already described, this bidirectional flow provides for a much enhanced deposition of the medicament in the posterior margin of the nasal cavity.

As will be understood, in essence, the present invention can be broadly based on any breath-actuated pressurized metered dose inhaler, where the usual mouthpiece is replaced by a nosepiece and a mouthpiece is provided in communication with the air inlet of the inhaler such as both to trigger the triggering mechanism and utilize the air exhaled by a subject as the entraining delivery air.

Finally, it will be understood that the present invention has been described in its preferred embodiments and can be modified in many different ways without departing from the scope of the invention as defined by the appended claims.

The invention claimed is:

1. A device for delivering a substance to the nasal airway of a subject, comprising:
   a flow resistor; and
   a delivery unit for delivering a substance in a gas flow to a nostril of the subject, wherein the delivery unit comprises a nosepiece shaped and sized for insertion into a nostril of the subject, a delivery channel fluidly connected to the nosepiece and configured to receive the substance to be delivered to the nostril, the nosepiece comprising an outlet through which a substance may be delivered into the nasal airway of the subject and a sealing member configured to seal the one nostril of the subject to the outlet, the sealing member including a frusto-conical portion and having a first, distal end and a second, proximal end and being enlarged towards the proximal end to cause an anterior region of the nasal cavity into which the nosepiece is inserted to be enlarged, and a dispensing unit driven by an exhalation air flow of the subject so as to supply a metered dose of substance from the dispensing unit into the delivery channel;
   wherein the device is configured to create a positive pressure differential between the oral cavity of the subject and the nasal airway of the subject when the subject exhales against the flow resistor, thereby indirectly achieving closure of the oropharyngeal velum of the subject, and the device is configured to deliver a substance entrained in a gas flow having a flow rate in the nasal airway of at least 20 liters per minute.

2. The device of claim 1, wherein the flow resistor is operably connected to a tubular section configured to be held between the lips of the subject.

3. The device of claim 1, wherein the flow resistor is operably connected to a mouthpiece.

4. The device of claim 1, further comprising:
   a pressure-triggered valve fluidly connected to the flow resistor, wherein the valve is configured to open when a predetermined positive pressure is developed upon exhalation by the subject.

5. The device of claim 1, wherein the nosepiece is formed of a resilient material.

6. The device of claim 1, wherein the nosepiece is configured to extend into a nasal cavity of the subject so as to expand the valve region of the nasal cavity of the subject.

7. The device of claim 1, further comprising:
   a positive pressure indicator or a flow rate indicator.

8. The device of claim 1, wherein the device is configured such that the gas flow entraining a substance is delivered at a driving pressure sufficient to cause the gas to flow around the posterior margin of the nasal septum of the subject and out of the other nostril of the subject.

9. The device of claim 1, wherein a portion of the nosepiece is shaped like a nasal olive, or comprises a nasal olive-like member, which is shaped and sized to create the fluid tight seal.

10. The device of claim 1, wherein the flow resistor is configured to deliver a substance entrained in a gas flow having a flow rate in the nasal airway of at least 20 liters per minute.

11. The device of claim 1, further comprising at least one of a delivery unit, control unit, pressure sensitive valve, mouthpiece, oral exhalation unit, flow resistor and valve, and movable element configured to deliver a substance entrained in a gas flow having a flow rate in the nasal airway of at least 20 liters per minute.

* * * * *